United States Patent [19]

Moise et al.

[11] Patent Number: 4,908,012
[45] Date of Patent: Mar. 13, 1990

[54] CHRONIC VENTRICULAR ASSIST SYSTEM

[75] Inventors: John C. Moise, Carmichael; Richard K. Wampler, Rancho Cordova; Kenneth C. Butler, Carmichael, all of Calif.

[73] Assignee: Nimbus Medical, Inc., Rancho Cordova, Calif.

[21] Appl. No.: 229,624

[22] Filed: Aug. 8, 1988

[51] Int. Cl.$^4$ .............................................. A61B 19/00
[52] U.S. Cl. ..................................... 600/16; 415/900; 417/356; 623/3; 604/151
[58] Field of Search ................ 415/900; 417/348–356; 600/16–18; 604/151; 623/3

[56] References Cited

U.S. PATENT DOCUMENTS

| | | | |
|---|---|---|---|
| 2,274,274 | 2/1942 | Pezzillo | 417/356 |
| 2,485,408 | 10/1949 | Pezzillo | 417/356 |
| 2,747,512 | 5/1956 | Fouché | 417/356 |
| 4,382,199 | 5/1983 | Isaacson | 623/3 |
| 4,625,712 | 12/1986 | Wampler | 604/151 |
| 4,688,998 | 8/1987 | Olsen et al. | 600/16 |
| 4,704,121 | 11/1987 | Moise | 623/3 |
| 4,763,032 | 8/1988 | Bramm et al. | 623/3 |
| 4,779,614 | 11/1988 | Moise | 600/16 |
| 4,817,586 | 4/1989 | Wampler | 604/151 |

OTHER PUBLICATIONS

Henig, *The Washington Post*, "Tiny Pump Gives Heart a Big Rest," 01/31/89.
Isaacson et al., Conference: Proceedings of the First Annual International Motorcon '81 Conference, Chicago, Il., Jun. 10–13, 1981.

*Primary Examiner*—Stephen C. Pellegrino
*Assistant Examiner*—Ralph Lewis
*Attorney, Agent, or Firm*—Weissenberger & Peterson

[57] ABSTRACT

An implantable ventricular assist system uses a small high-speed axial flow blood pump which may be grafted into the patient's circulatory system. The pump includes a blood tube in which the pump rotor and stator are coaxially contained, and a motor stator surrounding the blood duct. A permanent magnet motor rotor is integral with the pump rotor. Purge fluid for the hydrodynamic bearings of the device and power for the motor are preferably percutaneously introduced from extracorporeal sources worn by the patient. The purge fluid is introduced into the pump stator blades. This construction avoids the creation of discontinuities in the blood path wall due to the routing of drive power and/or fluid supply elements through the blood path wall. The described construction greatly reduces the size of the implant needed for a given blood flow rate and enhances its physiological compatibility with the body. Specifically, the system of this invention minimizes the risk of infection by reducing vibration, minimizing the size of the percutaneous conduit, and directing most of the heat generated by the pump into the blood.

12 Claims, 3 Drawing Sheets

CHRONIC VENTRICULAR ASSIST SYSTEM

FIELD OF THE INVENTION

This invention relates to an implantable continuous delivery ventricular assist system for patients with chronic cardiac disease, and more particularly to a system which does not require a discontinuity in the blood path wall for power transmission into the pump.

BACKGROUND OF THE INVENTION

Currently available ventricular assist systems using a continuous delivery blood pump, whether intravascular or implanted, have a common problem: somewhere in the system, the drive for the pump blades has to traverse the wall of the blood path. This is equally true of the shaft which drives the impeller of a centrifugal pump such as disclosed in U.S. Pat. No. 4,704,121 and of the drive cable of U.S. Pat. No. 4,625,712 which must traverse the wall of the femoral artery.

Wherever the drive traverses the wall of the blood path, a discontinuity exists which involves a danger of thrombus formation. Although this danger is substantially alleviated in centrifugal pumps by the invention disclosed in U.S. Pat. No. 4,704,121, it still exists in the physiologically much more desirable axial flow pumps.

Ideally, this problem can be solved by an axial flow pump with a magnetically suspended rotor, such as that proposed in copending application Ser. No. 07/036,304, which requires no bearing purge fluid supply and no penetration of the blood path wall; nor, for that matter, any percutaneous device. However, magnetically suspended blood pumps belong to a developing technology, and their commercial viability is still in the future.

A major problem with implanted cardiac assist devices is the almost universal emergence of infection when a device has been implanted for several months. It is believed that infection is related not only to sepsis of the percutaneous access, but also to the weight, relative motion and surface area of the device itself.

SUMMARY OF THE INVENTION

The present invention provides an implantable axial flow blood pumping system suitable for chronic ventricular assist which overcomes the above-described problems, yet whose construction and operation uses existing technology to advantage, and which can function with only a small percutaneous access for purge fluid and electrical power.

The pump of this invention avoids the need for a purge fluid supply to traverse the wall of the blood path by introducing the purge fluid into the pump stator through the interior of a stator blade. The need for torque transmission through the blood path wall is avoided by placing a permanent magnet rotor on the pump rotor (i.e. integrating the motor rotor with the rotatable pump element), and placing all motor windings outside the blood path. The incidence of infection is reduced because the inventive pump is an order of magnitude lighter and smaller, and less subject to motion or vibration, than previously known implantable blood pumps of the same capacity. Also, the small diameter (on the order of 3 mm) of the percutaneous access tube required minimizes the physiological stresses from that source.

The pump of this invention consists of a cylindrical blood tube in which a pump stator is coaxially suspended by a set of stator blades, one of which also serve as a conduit to convey purge fluid from the outside of the blood tube through the pump stator to the pump bearings. A hermetically sealed motor stator provides power to the pump rotor which is supported in the pump stator for rotation coaxially therewith.

The relative positions of the motor stator and rotor provide a very good heat conduction path from the motor stator iron into the blood. This is important for thermal management: tolerance of the implant is considerably improved by driving the heat generated by the motor into the blood rather than into the surrounding tissues.

The use of the short, straight blood tube and the use of an axial flow pump with common pump and motor bearings gives the inventive device a compactness, even at flow rates of 6 L/min or more, which greatly enhances its anatomic compatibility and allows it to be placed adjacent to the heart. Also, the absence of any eddy-causing obstructions or changes in flow direction throughout the device greatly reduces the likelihood of thrombus formation.

It is therefore the object of the invention to provide a very compact, high-flow implantable axial flow blood pump which is well tolerated by the body.

It is another object of the invention to provide an implantable ventricular assist system which has no drive or fluid supply elements traversing the wall of the blood path, and in which the heat generated by the motor is largely absorbed by the pumped blood.

It is a further object of the invention to provide an implantable blood pump system with percutaneous access in which the diameter of the required percutaneous access is minimized.

DESCRIPTION OF THE PREFERRED EMBODIMENT

Figure 1:
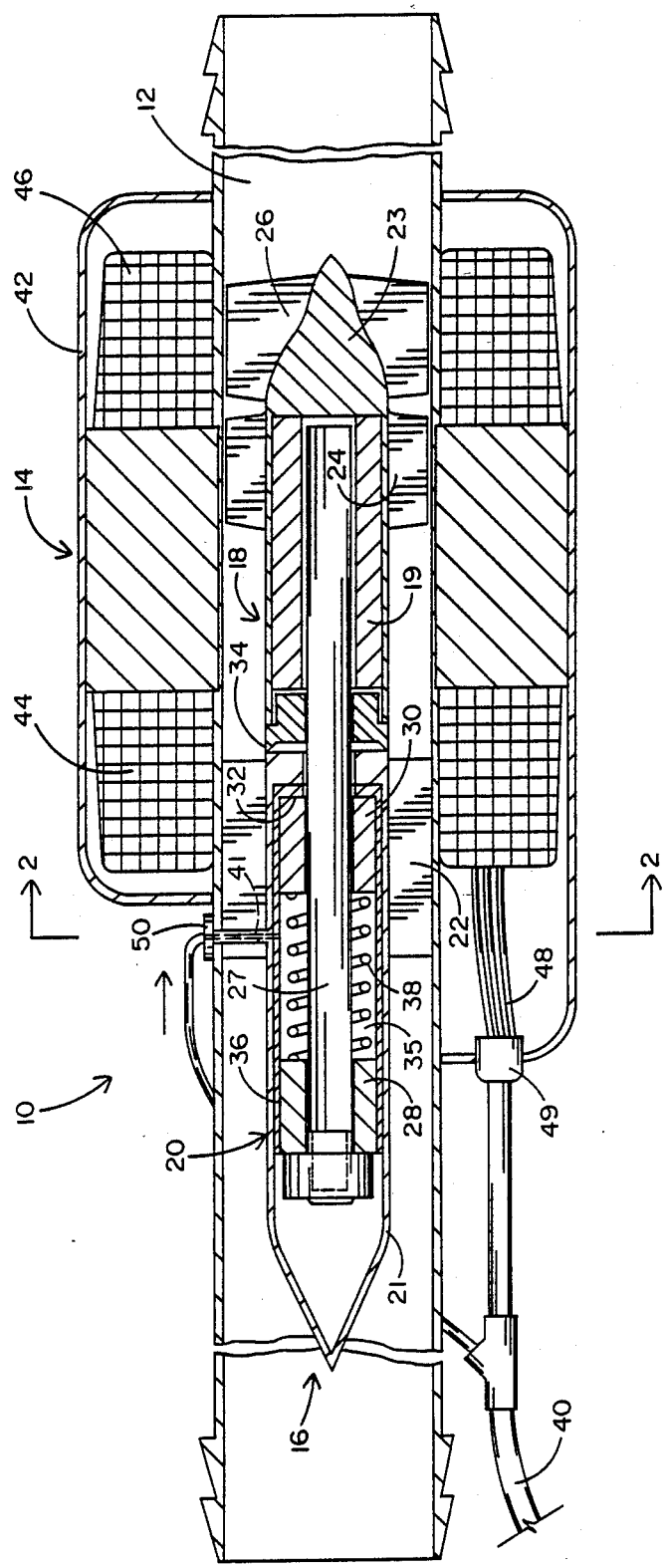
FIG. 1 is an axial section of one embodiment of the pump of this invention.
Figure 2:
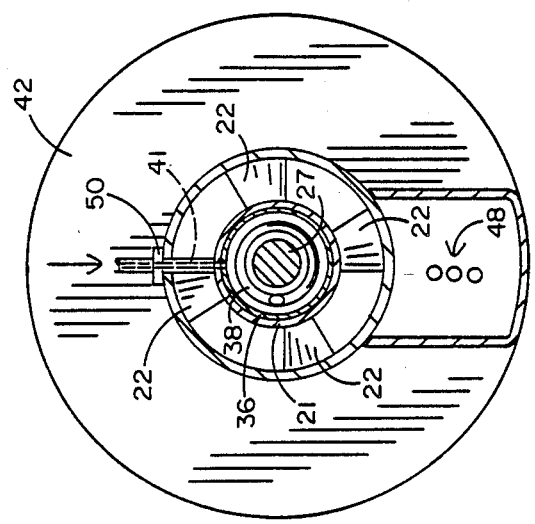
FIG. 2 is a transverse section along line 2—2 of FIG. 1.

The pump 10 depicted in FIGS. 1 and 2 essentially consists of a blood tube 12 surrounded by a hermetically sealed motor stator 14. An axial flow blood pump 16 is disposed coaxially within the blood tube 12 and forms therewith an annular blood duct which is a part of the blood path of the inventive system. The pump 16 is composed of a pump rotor 18 which includes the motor rotor 19 and blades 24, 26, and a pump stator 20 including a stator housing 21 which is fixedly mounted in the tube 12 by stator blades 22.

The pump rotor 18 has a hub 23 which carries one or more sets of rotor blades 24, 26, and which is mounted on a shaft 27 supported for rotation in pump stator 20 by a hydrodynamic journal bearing 28, and by a combined hydrodynamic journal and thrust bearing 30 fixed to the shaft 27. The outer surfaces of bearings 28 and 30 are preferably grooved for hydrodynamic reasons. Journal bearing 28 is slidably mounted in the cavity 35 formed by sleeve 36 within stator housing 21. The sleeve 36 is preferably made of a compatible bearing material because it can touch bearings 28 and 30 under startup or severe loading conditions. Spring 38 has a dual function: it biases bearing 30 into engagement with the inwardly directed end of sleeve 36, and the surfaces of face seal 34 against each other; and its torque also causes bearing 28 to rotate with shaft 27 even though it is not attached to the shaft 27.

A blood-compatible purge fluid (e.g. saline solution) for the hydrodynamic surfaces 28, 30 and 34 is supplied to the pump 10 from outside the patient's body through a lumen of the percutaneous conduit 40 which is connected to a passage 41 extending through one of the stator blades 22 and through housing 21 and sleeve 36 into the cavity 35. The purge fluid is discharged into the blood at face seal 34.

The motor stator 14 is enclosed in a hermetically sealed motor housing 42. the motor formed by motor stator 14 and motor rotor 19 is preferably a 3-phase brushless DC motor. Power is preferably supplied to the windings 44, 46 of the motor stator 14 from an extracorporeal power source, e.g. a power supply package carried by the patient, through appropriate wiring 48 extending through a second lumen of the percutaneous tube 40, and into the motor housing 42 through a fluid-tight seal 49. The purge fluid supply connection 50 is preferably located outside the housing 42 to prevent accidental leakage of saline fluid into the motor housing 42.

Inasmuch as most of the heat developed in the operation of the motor is generated in the motor and conveyed by the stator iron, the motor is effectively cooled by the blood and therefore imposes little thermal load on the tissues in which it is implanted. For that reason, and also because of the relatively vibration-free operation of an axial flow pump, the pump 10 is physiologically much more tolerable than prior art devices.

FIG. 2 illustrates the disposition of the stator blades 22. It will be understood that although four stator blades are shown, the number of stator blades used will depend upon the circumstances of a particular design and is not part of this invention.

Figure 3:
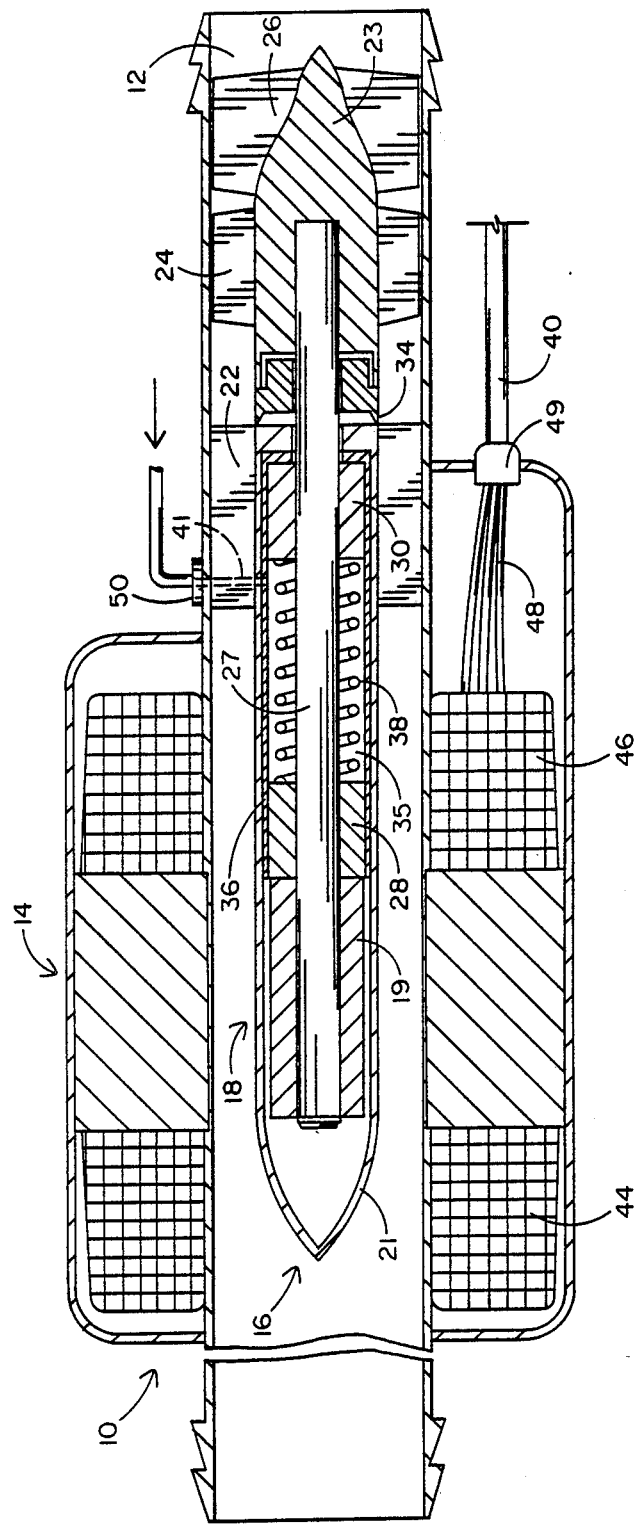
FIG. 3 is an axial section of another embodiment of the pump of this invention.

FIG. 3 shows an alternative embodiment of the device of this invention. In the embodiment of FIG. 3, the motor rotor is axially positioned within the pump stator housing 21, and the pump rotor portion axially outside the stator housing 21 merely carries the rotor blades.

In comparing the structures of FIGS. 1 and 3, it should be noted that in the embodiment of FIG. 1, where the motor rotor 19 is on the part of the pump rotor 18 which is cantilevered in the front of pump stator 20 (blood flows from right to left in FIGS. 1 and 3) and which is in direct contact with the blood, the rotational torque is transferred directly from the motor rotor to the rotor blades, and the bearings in the stator need only support the overhang load. On the other hand, the overhang bending moment is greater in the FIG. 1 embodiment because of the weight of the motor rotor and its distance from the bearings.

By contrast, the embodiment of FIG. 3 features a reduced overhang bending moment, and therefore imposes less load on the bearings. On the other hand, a significant clearance must be maintained in the configuration of FIG. 3 between the motor rotor 19 and the stator housing 21 to minimize fluid losses. This increases the magnetic gap between the motor stator and rotor, and the electromagnetic losses associated therewith. In the embodiment of FIG. 3, the structure of the pump 10 is the same as that described above in connection with FIG. 1, except that the motor rotor 20 is positioned at the left end of shaft 27 within the stator housing 21. This allows the overhanging rotor hub 23 to be made shorter, thus providing a better balance and imposing less of a bending moment on shaft 27.

Figure 4:
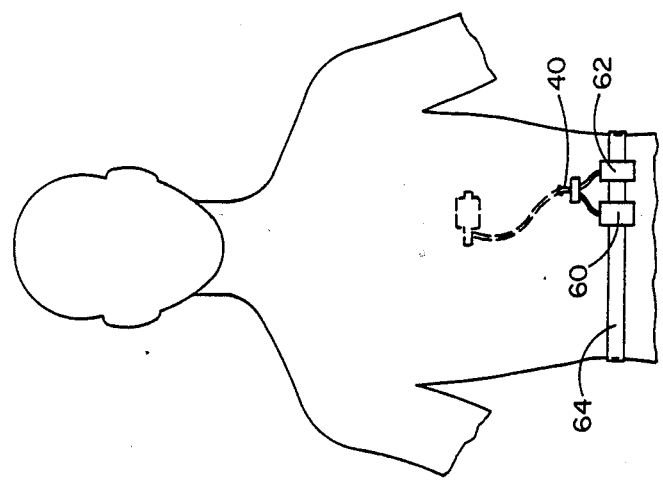
FIG. 4 is a schematic illustration showing the percutaneous purge fluid and power supplies of the preferred embodiment of the invention.

The pump of this invention can be used in several different ways. In its preferred embodiment, the sources of purge fluid and electrical power for the motor may, as shown in FIG. 4, be a constant-volume fluid supply and delivery device 60 and a motor power supply 62 including a power source and the necessary electronics for controlling the motor. The devices 60 and 62 may be carried by the patient on an appropriate belt 64.

We claim:

1. An implantable ventricular assist system for patients with chronic cardiac disease, comprising:
    (a) a blood pump including a blood tube adapted to form a part of a blood path within said patient;
    (b) a pump stator mounted coaxially within said blood tube to form an annular blood duct within said tube, said pump stator being mounted within said blood tube by a plurality of stator blades;
    (c) a pump rotor supported for rotation in said pump stator on hydrodynamic bearings, said pump rotor and pump stator together defining with said blood tube a smooth annular blood path around said pump rotor and pump stator;
    (d) a permanent magnet motor rotor integral with said pump rotor;
    (e) a motor stator encircling said blood tube radially adjacent said motor rotor; and
    (f) means wholly external of said tube for transmitting electrical power from an extracorporeal source to said motor stator;
    (g) whereby said power transmitting means do not create any discontinuity in the wall of said blood path.

2. The system of claim 1, further comprising:
    (h) a source of purge fluid for said hydrodynamic bearings, said purge fluid source being located outside said blood tube;
    (i) means for supplying purge fluid to said bearings from said purge fluid source through one of said stator blades; and
    (j) whereby said purge fluid supply means do not create any discontinuity in the wall of said blood path.

3. The system of claim 1, in which the iron of said motor stator has a major surface in thermally conductive relation with the blood in said blood tube, whereby said motor stator is cooled by said blood.

4. The system of claim 1, in which said motor rotor is positioned on a portion of said pump rotor which is in direct contact with the blood in said annular blood duct.

5. The system of claim 4, in which said pump rotor portion is cantilevered in front of said pump stator.

6. The system of claim 1, in which said motor rotor is positioned on a portion of said pump rotor located inside said pump stator.

7. An implantable chronic ventricular assist system, comprising:
    (a) an axial flow pump including:
        (i) a substantially cylindrical blood tube;
        (ii) a substantially cylindrical pump stator, said pump stator including a plurality of stator blades, said stator blades being fixed to said blood tube and said pump stator so as to support said pump stator coaxially within said blood tube;

(iii) a pump rotor including a shaft journalled in said pump stator on hydrodynamic bearings so as to support said pump rotor coaxially within said blood tube, said pump rotor carrying a motor rotor and a plurality of rotor blades within said blood tube;

(iv) a sealed motor housing surrounding a portion of said blood tube, and (v) a motor stator disposed within said housing, said motor stator encircling said blood tube radially adjacent said motor rotor; and (b) means for supplying purge fluid to said bearings, and electrical power to said motor stator, said purge fluid supplying means including a purge fluid supply passage from the outside of said blood duct to the interior of said pump stator through one of said stator blades.

8. The system of claim 7, in which said purge fluid is discharged into said blood tube at an interface between said pump stator and said pump rotor.

9. The system of claim 8, in which the end of said supply passage outside of said blood tube is located outside said motor housing.

10. The system of claim 7, in which said purge fluid supply means include
(i) an extracorporeal purge fluid source;
(ii) percutaneous fluid connection means connectable to said purge fluid source to convey purge fluid from said source into the patient's body; and
(iii) purge fluid conduit means adapted to be implanted in a patient, said purge fluid conduit means being connected to said percutaneous fluid connection means and said supply passage for conveying purge fluid from said source to said pump stator.

11. The system of claim 7, in which said electrical power supply means include cabling means adapted to be implanted in a patient, said cabling means extending from an extracorporeal location to said pump and entering said motor housing through a fluid-tight seal for connection to said motor stator.

12. The system of claim 7, in which said purge fluid and power supply means include a single percutaneous conduit for percutaneously conveying both power and purge fluid.

* * * * *